United States Patent [19]
Jorneus et al.

[11] Patent Number: 5,662,474
[45] Date of Patent: Sep. 2, 1997

[54] SPACING MEMBER FOR TOOTH IMPLANT

[75] Inventors: Lars Jorneus, Riabergsvagen; Anders Boss, Krokslatts Parkgata; Halvar Hanssen, Runslingan, all of Sweden

[73] Assignee: Nobel Biocare AB, Goteborg, Sweden

[21] Appl. No.: 530,121

[22] PCT Filed: Feb. 9, 1995

[86] PCT No.: PCT/SE95/00131

§ 371 Date: Dec. 5, 1995

§ 102(e) Date: Dec. 5, 1995

[87] PCT Pub. No.: WO95/21589

PCT Pub. Date: Aug. 17, 1995

[30] Foreign Application Priority Data

Feb. 11, 1994 [SE] Sweden .................................. 9400448

[51] Int. Cl.⁶ .......................... A61C 13/12; A61C 13/225; A61C 8/00
[52] U.S. Cl. .............................. 433/172; 433/173
[58] Field of Search .......................... 433/172, 173, 433/174, 175, 176

[56] References Cited

U.S. PATENT DOCUMENTS

| | | |
|---|---|---|
| 4,793,808 | 12/1988 | Kirsch . |
| 4,872,839 | 10/1989 | Brajnovic ........................ 433/173 |
| 4,907,969 | 3/1990 | Ward ................................ 433/173 |
| 5,000,685 | 3/1991 | Brajnovic ........................ 433/173 |
| 5,069,622 | 12/1991 | Rangert et al. . |
| 5,087,200 | 2/1992 | Brajnovic et al. ............... 433/173 |
| 5,145,372 | 9/1992 | Daftary et al. ................... 433/173 |
| 5,209,666 | 5/1993 | Balfour et al. ................... 433/173 |
| 5,213,502 | 5/1993 | Daftary ............................. 433/172 |
| 5,238,405 | 8/1993 | Marlin ........................ 433/172 X |
| 5,362,235 | 11/1994 | Daftary ............................. 433/172 |
| 5,431,567 | 7/1995 | Daftary ............................. 433/172 |

*Primary Examiner*—Nicholas D. Lucchesi
*Attorney, Agent, or Firm*—Pollock, Vande Sande & Priddy

[57] ABSTRACT

The invention relates to a spacing member for a tooth implant, comprising a base portion for attachment to a fixture implanted in the jawbone, and an upper part with an essentially conical outer limit surface for attachment to a tooth prosthesis. The base portion comprises a through hole for a spacing screw which is intended to engage with an internally threaded bore in the upper portion of the fixture and thereby form a first screw connection for locking the spacing member securely in a defined direction of deflection in relation to the fixture. The upper part comprises a second screw connection for attachment of the tooth prosthesis, which screw connection forms a fixed angle δ in relation to the first screw connection. The upper part of the inlet opening for the through hole which is formed in the conical outer limit surface in the upper part of the spacing member, and through which opening the spacing screw is intended to be introduced during assembly, is offset towards the line of symmetry of the through hole. In this way, the height of the spacer can be kept low, even in those cases where the fixed angle δ between the two screw connections is comparatively small, preferably within the range of 15°–25°.

6 Claims, 2 Drawing Sheets

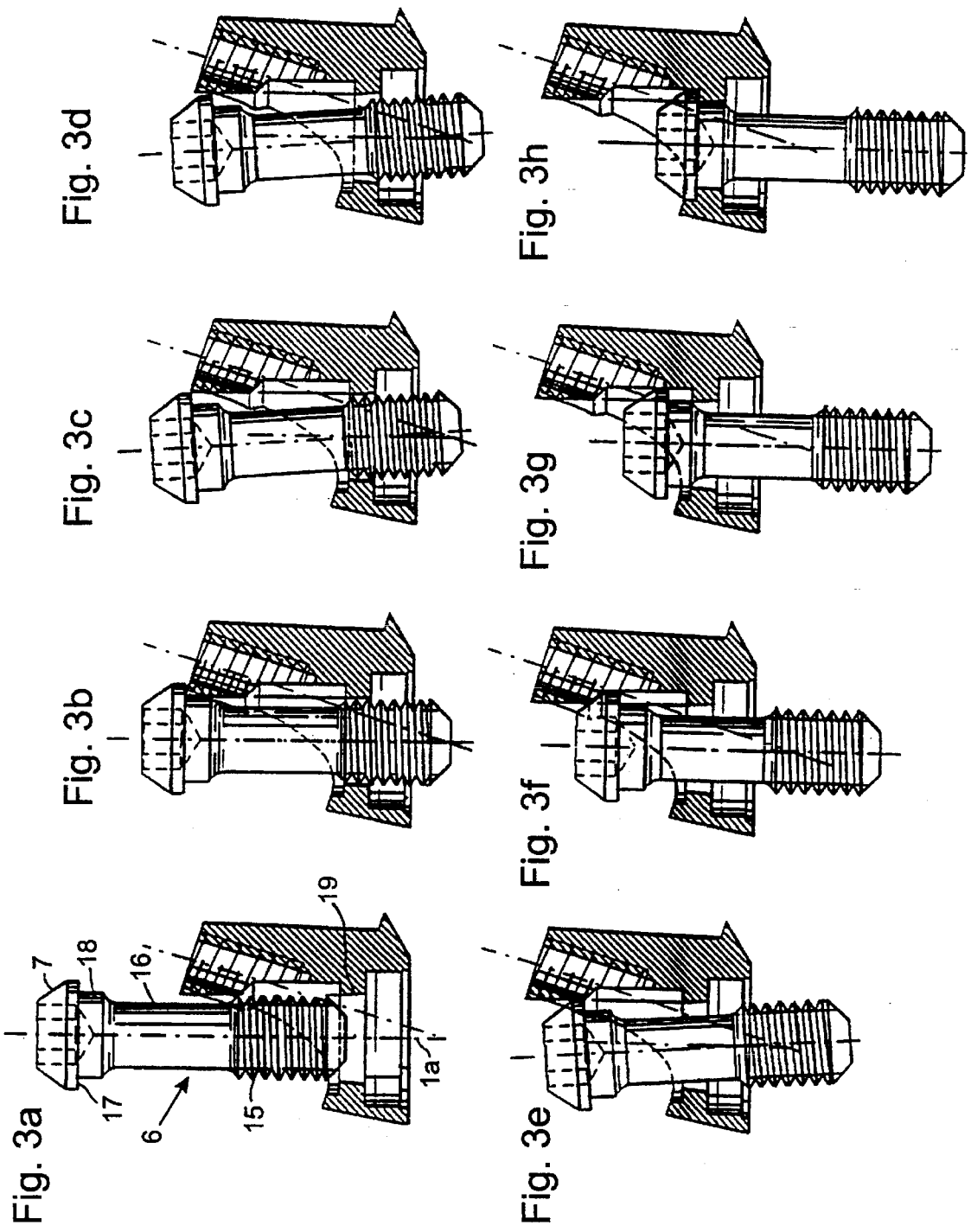

SPACING MEMBER FOR TOOTH IMPLANT

FIELD OF THE INVENTION

The present invention relates to a spacing member for a tooth implant, comprising a base portion for attachment to a fixture implanted in the jawbone, and an upper part with an essentially conical outer surface for attachment of a tooth prosthesis. The base portion comprises a through hole for a spacing screw intended to engage with an internally threaded bore in the upper portion of the fixture to thereby form a first screw connection for locking the spacing member securely in a defined direction of deflection in relation to the fixture. The upper part comprises a second screw connection for attachment of the tooth prosthesis, which screw connection forms a fixed angle in relation to the first screw connection.

BACKGROUND OF THE INVENTION

The reason why angled spacers have been introduced in some cases is that with conventional implant systems the securing screw for the tooth bridge can sometimes end up in an unsuitable position. By means of an angled spacer, the securing screw can be placed in a position which is more favorable from the point of view of appearance and from the point of view of dental technique.

Many of the previously known angled spacers are also adjustable, although in many cases this is a disadvantage since it is difficult to recover the exact position if the setting becomes loose, and to get a tooth bridge into place if the setting has been dislodged. In addition, certain constructions of this type are weak and offer poor resistance due to the fact that they have been made up of a ball with a narrow neck. Another disadvantage of these previously known constructions has been that pockets exist in which bacteria can gather and give rise to inflammations.

Angled spacers with a fixed angle between the fixture and the prosthetic attachment screw are also already known, for example, from EP 0 323 421. In this patent the spacing member is designed as a single part and has a conical base portion which can be securely locked in a defined direction of deflection in relation to the fixture by means of a first screw connection, a segment-shaped intermediate part, and a conical upper part with a second screw connection for attachment of the tooth prosthesis, the second screw connection forming a fixed angle, preferably within the range of 25°–40°, in relation to the first screw connection. An angled spacer of this type is strong, comprises few parts and makes it easy for the prosthodontist to recover the correct position should the setting come loose. However, in their present form, the angled spacers with a fixed angle also have certain limitations. These limitations are that the angle is too great in many clinical cases. The existing angled spacer may have an angle of about 30°, whereas a more desirable angle would be about 15°. To achieve this using today's basic solution, the upper conical attachment part must be made very much higher in order to provide room for the internal thread in the upper conical part. Such an increase in height is not desirable, since this would severely limit the usability of the component. Other conceivable solutions, such as, for example, an asymmetrically positioned hole in the upper conical attachment part, may be possible, but these have the result that a number of components then also become asymmetrical and are thereby difficult to manufacture and to use without losing the precision in the subsequent laboratory work.

Another limitation of existing angled spacers is that the spacer height is too great to permit a satisfactory aesthetic appearance in a relatively large number of cases. This problem can be solved by reducing the angle. However, the screw head on the screw which secures the spacer to the fixture then gets in the way of the conical cap which is secured over the spacer.

SUMMARY OF THE INVENTION

An object of the invention is therefore to solve the above problems and to provide an angled spacer which exhibits a smaller angle than previously, but in which today's basic solution, as regards a base portion and an upper attachment part formed in a single piece, can be retained, and which in addition is relatively simple to manufacture using current machining methods.

BRIEF DESCRIPTION OF THE DRAWINGS

The invention will be described in greater detail hereinbelow with reference to the attached drawings, in which

FIG. 3 shows how the spacing member cooperates with a spacing screw for attachment of the spacing member to a tooth implant (fixture)

DETAILED DESCRIPTION OF THE PREFERRED EMBODIMENT

Figure 1:
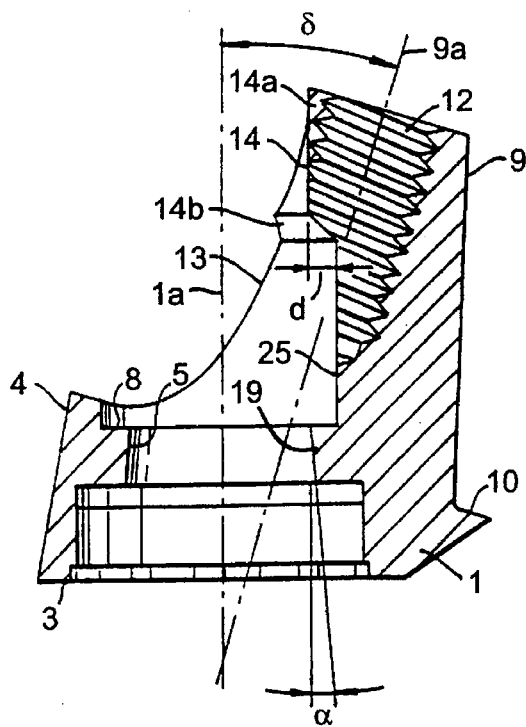
FIG. 1 shows a sectional side view of the angled spacing member.
Figure 2:
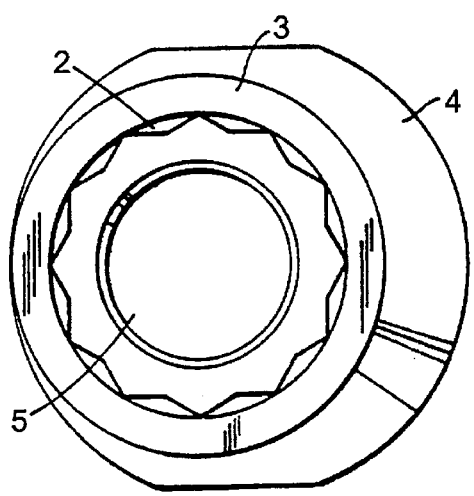
FIG. 2 shows an end view of the base portion of the spacing member.

As is evident from FIGS. 1 and 2, the spacing member comprises a mainly downwardly narrowing, essentially conically shaped base portion 1 intended to cooperate with the upper portion of a fixture of the type which comprises an upper hexagon. Fixtures of this kind are already known and will therefore not be dealt with in detail here. The base portion is arranged such that its line of symmetry (center line) 1a coincides with the line of symmetry of the fixture. The base portion is further formed with an internal twelve-pointed geometry 2 which fits against the hexagon of the fixture, such that the spacing member, when turned, moves 30° instead of 60° between the directions of deflection. The twelve-pointed geometry 2 in this way constitutes a rotational lock and provides twelve fixed directions of deflection for the spacing member. The base portion has an outer annular support surface 3 which bears against the shoulder portion of the fixture. The conical outer surface 4 connects with an even fit to the upper cylindrical side surface of the fixture, so that the surface below the gum level is completely smooth.

The base portion further comprises a through hole 5 for a spacing screw 6, see also FIG. 3, which engages with the internally threaded bore in the upper portion of the fixture in order to lock the spacing member securely to the fixture. The hole 5 consists of a narrower cylindrical or conical part 19 and of a cylindrical widened part 25, the head 7 of the spacing screw, after it has been tightened, bearing against an upper, internal circular heel 8 in the spacing member between the narrower part and the widened part of the hole 5.

The base portion 1 of the spacing member thus corresponds in principle to the base portion of the spacing member which is shown in EP 0 323 421. However, in order to permit a smaller height of the spacer, the base portion merges at the top directly into a conical upper part 9 for attachment of the prosthetic construction. The line of symmetry 9a of the conical upper pat forms an angle δ with the line of symmetry 1a of the base portion. The deflection angle δ preferably lies within the range of 15°–20°, in this embodiment 17°. The base of the conical upper part 9 merges with the base portion 1 via an annular collar 10 which forms a support for a conical cap 11, see also FIG. 4.

The conical upper part 9 is provided with a threaded hole 12 for the screw connection which joins the spacing member to the conical cap 11 cast into the tooth bridge. The screw connection is thus coaxial with this cap. The outer surface of the conical upper part further comprises an inlet opening 13 for the spacing screw 6 so that the latter can be guided down through the hole 5 and screwed firmly in the fixture with the aid of a screwdriver which is also guided down through the inlet hole in the axial direction of the screw for the purpose of tightening the screw connection. In contrast to the previously known spacing member in EP 0 323 421, the inlet opening 13 is not a straight cylindrical hole forming a continuation of the cylindrical widened part 25 through the base portion 1, but instead the upper part 14 of the inlet opening is offset towards the center line 1a of the hole 5. By means of this offset of the upper part 14 of the inlet opening in the conical outer surface, the material 14a remaining in the upper portion of the conical upper part is still sufficient for the threaded hole 12 for securing of the conical cap to be bored with a sufficient material thickness all round, despite the low angle of 15°–25°. It is clear from FIG. 1 that if the inlet opening 13 were to have formed a direct continuation of the cylindrical widened part 25, then the wall between the threaded hole 12 and the inlet opening 13 would also have been broken through. The offset d of the upper part 14 of the inlet opening is preferably adapted to a straight screwdriver of known construction for tightening the screw connection, i.e. the offset of the upper part 14 of the inlet opening in towards the center line of the hole is not so great that the screwdriver cannot be guided in the axial direction down through the hole for the purpose of tightening the screw connection. In the example shown in FIG. 1, the offset d of the upper part 14 of the inlet opening corresponds to the width of the circular heel 8 for the head of the spacing screw and in this case the inlet opening cuts in somewhat through the plane top surface of the conical upper part 9.

The offset d of the upper part 14 of the inlet opening can also be greater, so that the inlet opening is situated completely in the conical outer surface of the upper part 9. In this case an angled screwdriver has to be used for tightening the screw connection. The screwdriver is in this case guided in through the opening in the conical limit surface at an angle which essentially corresponds to the angle δ between the two screw connections.

The spacing screw 6 comprises a lower threaded portion 15 arranged to engage in the upper thread of the fixture, an elongate middle area 16, and a screw head 7 with a heel 17 underneath for bearing against the inner circular heel 8 in the spacing member. The head 7 of the spacing screw merges with the middle area 16 via a short cylindrical portion 18 of slightly larger diameter. FIG. 3 shows, step by step, how the spacing screw is guided through the hole 5 of the spacing member for attachment to the fixture. It is clear form FIGS. 3a and b that the direction of the spacing screw, then it is guided in through the spacing member, first coincides with the line of symmetry 1a. Since the upper part 14 of the inlet opening has been offset, the spacing screw 6 has to be angled slightly as its head 7 passes the inlet opening, see FIGS. 3c, d and e. As soon as the head of the spacing screw has passed through the inlet opening, its direction of introduction then once more coincides with the line of symmetry 1a, see FIGS. 3f, g and h. In FIG. 3h the spacing screw is in place and bears against the circular heel 8 with its head. In order to permit the angled positioning when the screw is being passed through the narrower part 19 of the hole 5 under the circular heel, i.e. under the screw head 7, this hole 19 is conical, i.e. it has a downwardly increasing diameter, see FIGS. 3c, d and f. Without such conicity there would be a risk of clamping occurring, or alternatively the diameter of the hole would have to be increased, resulting in a reduction in the width of the circular heel 8, which would nevertheless increase the risk of material deformations occurring upon tightening of the screw connection. In this embodiment the cone angle is about 5°.

The screw head 7 of the spacing screw 6 is conical, narrowing towards the top, for two reasons: on the one hand, the introduction of the spacing screw part the offset inlet opening is facilitated if the maximum width of the screw head is kept short, and, on the other hand, a cylindrical screw head would extend beyond the conical limit surface of the spacing member if, for aesthetic reasons, a small spacer height was needed. This is shown most clearly in FIG. 3h and in FIG. 4 where a previously known circular-symmetrical, conical cap 11 has been attached to the spacing member with the aid of a screw 20 which engages in the upper threaded hole 12. The cap rests with its wider, outwardly curved part 21 against the annular support surface 10 of the spacing member, and it additionally has the same function as the attachment sleeve 16 which is described in the EP 0 323 421.

Figure 4:
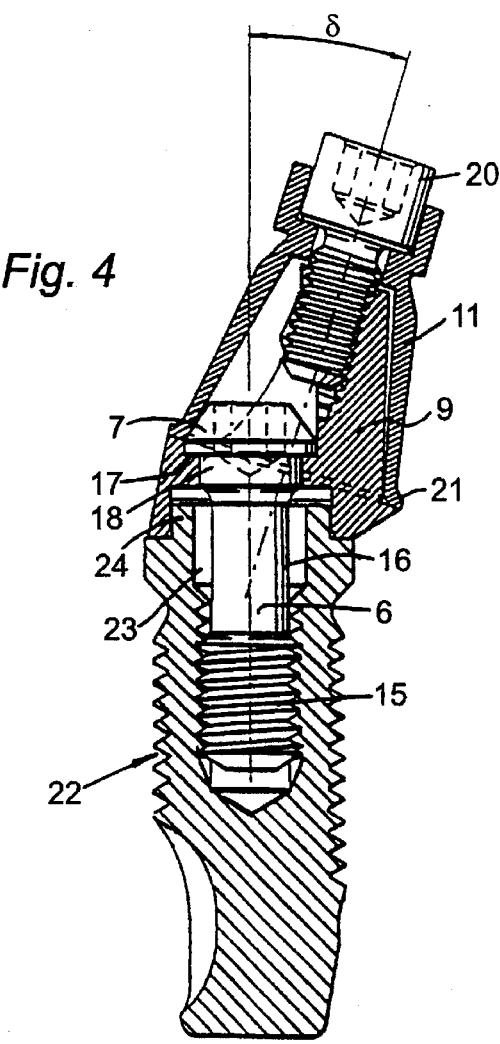
FIG. 4 shows the spacing member joined together with the fixture, and an attachment sleeve in the form of a conical cap for attachment of a tooth prosthesis.

It is clear from FIG. 4 that the overall height of the spacing member with attachment sleeve is extremely small. Despite the low angle, 15°–20°, the construction permits two screw connections, and the attachment sleeve does not need to be cemented firmly onto the spacer, a solution which was formerly used. The fixture 22 is of known construction, with an upper bore 23 for the spacing screw and an upper hexagon 24 which cooperates with the inner, twelve-pointed geometry 2, see above.

The spacing member is comparatively simple to manufacture. In a first drilling operation, a through hole with a fairly small diameter is formed, which corresponds to the narrow hole 19. The cylindrical widened part 25 is formed, in a second machining operation, by means of the diameter in the base portion of the hole and in its upper part being extended up to a certain distance from the end plane of the conical upper part, where the hole merges with the narrower diameter via a collar 14b. The result of this operation is therefore that the upper part of the through hole is offset in parallel, by a distance d, towards the center line of the hole.

The invention is not limited to the embodiment shown above by way of example, but instead can be varied within the scope of the patent claims which follow. A particular point to note is that the essentially conical limit surface of the upper part of the spacing member can have different appearances, for example it can be stepped in shape, as long as it is accommodated within the conical cap which is secured over the spacer.

We claim:

1. A spacing member for an angulated prosthetic tooth implant removably attachable to an embedded threaded fixture:

said spacing member having first and second intersecting through bores, the first of said through bores having its axis parallel with that of the threaded fixture to enable detachable fixation of said spacing member to said fixture by means of a threaded screw passing through said first through bore and threadably engaging with a threaded bore in said fixture, the second of said through bores having its axis inclined at an acute angle to said first through bore to enable detachable fixation of the angulated tooth implant with said spacing member, said first through bore having an upper portion laterally offset from a lower portion in a direction opposite to the direction in which said second through bore is inclined to thereby enable removable fixation of the spacing member to the fixture.

2. The spacing member as claimed in claim 1 in which said screw has a conically shaped head tapering inwardly at its end portion protruding outwardly from the threaded bore in said fixture, whereby said outwardly extending portion does not extend beyond the conically shaped limiting surface of the spacing member when installed.

3. Spacing member according to Patent claim 1, characterized in that the offset of the upper part (14) of the inlet opening is adapted to a straight screwdriver, so that the latter can be guided in the axial direction down through the hole (5) for the purpose of tightening the first screw connection.

4. Spacing member according to Patent claim 3, characterized in that the through hole (5) comprises a narrower part (19) and a cylindrical widened part (25) so that an inner circular heel (8) is formed against which the screw head (7) of the spacing screw bears when the spacing member is locked securely to the fixture, the said offset of the upper part (14) of the inlet opening corresponding to the width of the circular heel (8).

5. Spacing member according to Patent claim 1, characterized in that the narrower part (19) of the through hole (5), i.e. the hole under the head (7) of the spacing screw, is conical and widens towards the bottom, so as to make it possible to guide the spacing screw (6) down through the hole in an oblique direction.

6. Spacing member according to Patent claim 1, characterized in that the offset of the upper part (14) of the inlet opening is chosen such that the inlet opening (13) is situated completely in the conical limit surface of the upper part (9) of the spacing member for adaptation to an angled screwdriver for the purpose of tightening the first screw connection.

* * * * *

UNITED STATES PATENT AND TRADEMARK OFFICE
CERTIFICATE OF CORRECTION

PATENT NO. : 5,662,474
DATED : September 2, 1997
INVENTOR(S): JORNEUS et al.

It is certified that error appears in the above-identified patent and that said Letters Patent is hereby corrected as shown below:

On the title page, item [75] Inventors change "Riabergsvagen" to
    ---Riabergsvagen 7B, S-430 30 Frillesas---;

change "Krokslatts Parkgata"
    to ---Krokslatts Parkgata 13, S-431 68 Molndal---;

change "Runslingan"
    to ---Runslingan 115, S-423 47 Torslanda---;

Signed and Sealed this

Ninth Day of December, 1997

*Attest:*

BRUCE LEHMAN

*Attesting Officer*     *Commissioner of Patents and Trademarks*